(12) United States Patent
Zimmer et al.

(10) Patent No.: US 6,881,378 B1
(45) Date of Patent: Apr. 19, 2005

(54) MULTILAYERED ANALYTICAL DEVICE

(75) Inventors: Volker Zimmer, Dossenheim (DE); Hans-Peter Braun, Weinheim (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/528,158

(22) Filed: Mar. 17, 2000

(30) Foreign Application Priority Data

Mar. 19, 1999 (DE) .......................................... 199 12 365

(51) Int. Cl.[7] .............................................. G01N 31/22
(52) U.S. Cl. .............................. 422/58; 422/56; 422/61; 436/166; 436/169; 436/170
(58) Field of Search .............................. 422/56, 58, 61; 436/164, 166, 168–170

(56) References Cited

U.S. PATENT DOCUMENTS

| | | | |
|---|---|---|---|
| 4,220,713 A | 9/1980 | Rittersdorf et al. ............ | 435/14 |
| 4,301,115 A | 11/1981 | Rapkin et al. ................. | 422/56 |
| 4,477,575 A | 10/1984 | Vogel et al. .................. | 436/170 |
| 4,806,312 A | * 2/1989 | Greenquist .................... | 422/56 |
| 4,861,711 A | 8/1989 | Friesen et al. ................. | 436/7 |
| 5,071,746 A | 12/1991 | Wilk et al. ................... | 435/7.94 |
| 5,089,103 A | 2/1992 | Swedberg .................. | 204/182.8 |
| 5,096,836 A | 3/1992 | Macho et al. ................ | 436/169 |
| 5,248,708 A | 9/1993 | Uemura et al. ............. | 523/212 |
| 5,451,504 A | 9/1995 | Fitzpatrick et al. ........... | 435/7.2 |
| 5,470,757 A | * 11/1995 | Gagnon et al. .............. | 436/164 |
| 5,783,759 A | 7/1998 | Wielinger et al. ........ | 73/864.72 |
| 5,827,477 A | 10/1998 | Macho et al. ................. | 422/56 |
| 5,846,837 A | 12/1998 | Thym et al. .................. | 436/170 |
| 5,899,856 A | * 5/1999 | Schoendorfer et al. ...... | 600/362 |
| 6,036,919 A | 3/2000 | Thym et al. .................... | 422/58 |
| 6,207,000 B1 | 3/2001 | Schwobel | |
| 6,244,208 B1 | * 6/2001 | Qui et al. ..................... | 116/207 |
| 6,335,205 B1 | * 1/2002 | Bausback .................... | 436/514 |
| 6,514,773 B1 | 2/2003 | Klein et al. | |

FOREIGN PATENT DOCUMENTS

| | | | |
|---|---|---|---|
| CA | 2118435 A1 | 4/1995 | ......... G01N/33/543 |
| CA | 2154620 A1 | 1/1996 | ......... G01N/33/558 |
| EP | 0 138 152 A2 | 4/1985 | ......... G01N/21/03 |
| EP | 0 174 188 A2 | 3/1986 | ......... B65D/81/34 |
| EP | 0 212 314 A2 | 3/1987 | ............. B01L/3/00 |
| EP | 0 297 390 | 1/1989 | |
| EP | 0 359 831 B1 | 3/1990 | |
| EP | 0 471 986 A2 | 2/1992 | ............ C12M/1/40 |
| EP | 0 699 906 | 3/1996 | |
| EP | 0 750 185 | 6/1996 | |
| EP | 0 821 233 | 1/1998 | |
| EP | 0 821 234 | 1/1998 | |
| GB | 1512352 | 6/1978 | ........... A24B/15/00 |
| HU | 206918 | 1/1993 | |
| HU | P9701273 | 8/1998 | |
| WO | WO 89/05457 | 6/1989 | |
| WO | WO 92/08972 | 5/1992 | |
| WO | WO97/27483 | 7/1997 | ......... G01N/33/546 |

OTHER PUBLICATIONS

Abstract entitled, "Laminated packaging material for fruit and vegetables," JP56010458A (1981).
Abstract entitled, "Material for retaining freshness of vegetables and fruits," JP56010459 A (1981).
Abstract entitled, "Pressure–sensitive adhesive compsn.," JP02011684 (1990).
Abstract entitled, "New antistatic adhesive," Zhongguo Jia-onianji (1995).

* cited by examiner

*Primary Examiner*—Lyle A. Alexander
(74) *Attorney, Agent, or Firm*—Jill L. Woodburn; Richard T. Knauer; Sujatha Subramaniam

(57) ABSTRACT

The invention concerns an analytical device containing at least two components in which at least two of the components are joined together with the aid of an adhesive, which is characterized in that the adhesive contains an adsorptive material. The invention additionally concerns the use of adhesives which contain adsorptive material to manufacture analytical devices.

26 Claims, 1 Drawing Sheet

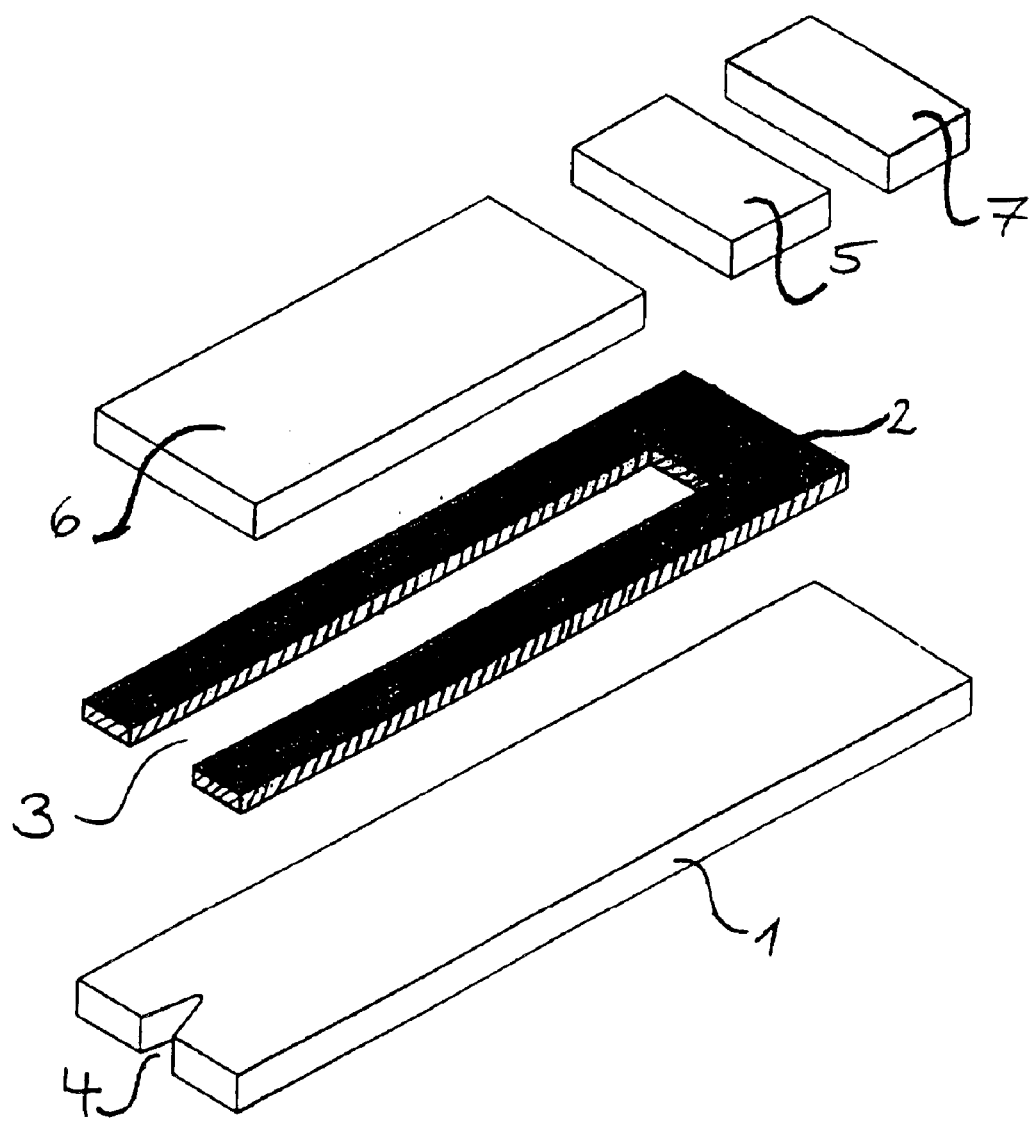

MULTILAYERED ANALYTICAL DEVICE

The invention concerns an analytical device such as an analytical test element containing at least two components wherein at least two of the components are joined together with the aid of an adhesive.

So-called carrier-bound tests (test carriers, test elements, test strips) are often used for the rapid and simple, qualitative or quantitative analytical determination of components of liquid samples e.g. aqueous body fluids such as blood, serum or urine. In these carrier-bound tests the detection reagents are embedded in corresponding layers of a carrier which is brought into contact with the liquid sample. The reaction of the liquid sample and reagents leads to a detectable signal when a target analyte is present e.g. a measurable electrical signal or a colour change which can be evaluated visually or with the aid of an instrument e.g. by reflection photometry.

Analytical test elements or test carriers are frequently constructed as test strips which are essentially composed of an elongate carrier material made of plastic and detection layers as test fields which are mounted thereon. In many cases the test elements are assembled by welding or glueing the carrier material and detection layer. In particular welding by means of ultrasound and glueing with hot-melt adhesives (so-called hotmelts), cold-setting adhesives or adhesive tapes have proven to be advantageous for the manufacture of large numbers of test elements, and adhesive tapes are being used more often for the manufacture due to the potential high production rate. Test elements that are manufactured using adhesives are for example described in the German Patent Applications with the file numbers P 197 53 847.9 and P 198 15 684.7 and in EP-A 0 212 314, EP-A-0 297 390, EP-A-0 297 389, EP-A 0821 234 and EP-A 0 821 233.

Although the manufacture of analytical test elements with the aid of adhesives is wide-spread, problems occasionally occur with the test elements which are related to the use of adhesives. In particular it is known that adhesives can have adverse effects on the stability of test elements. In this case it is assumed that ingredients of the adhesives that are used to bond the individual test element components have a negative effect on the stability of the reagents in the detection layer. Therefore when optimizing the test element stability one tries, among other things, to minimize stability problems by a suitable selection of the adhesives that are used. An optimum choice of adhesive can be very time-consuming and costly due to the very different and sometimes very sensitive reagents in the detection layers and the great diversity of adhesives that are in principle available for test element manufacture.

Analytical test elements for aqueous sample liquids such as body fluids are often treated chemically and/or physically in those areas which are to be wetted by the sample material, e.g. in the area of the detection layer, in order to facilitate the wetting. For example it is known from the German Patent Application file number P 197 53 848.7 that hydrophobic i.e. water-repellent surfaces can be made hydrophilic by treatment with wetting agents or by coating with oxidized aluminium which facilitates wetting of the surfaces with aqueous sample liquids or makes it possible to do this. Surfaces treated in this manner in test elements also exhibit stability problems in the presence of adhesives which are manifested as a poor wettability with aqueous liquids. This problem does not only occur with test elements but is also of interest for other analytical devices in which wetting of surfaces plays a role e.g. sampling elements, cuvettes or such like. It applies in particular when liquid uptake into the analytical device occurs with the aid of capillary forces.

The object of the invention is to eliminate the disadvantages of the prior art. In particular an object of the present invention is to increase the stability of analytical devices, in particular test elements, in which adhesives are used to assemble the individual components.

This object is achieved by the subject matter of the invention as characterized in the patent claims.

The invention concerns an analytical device containing at least two components in which at least two of the components are joined together with the aid of an adhesive characterized in that the adhesive contains an adsorptive material.

The analytical devices according to the invention are preferably suitable for use with sample liquids. However, it is also possible to use them to examine solid or gaseous substances provided these substances are contacted before or during the analysis with a liquid reaction medium such as a buffer and are dissolved or suspended in it. Suitable sample liquids are in particular aqueous liquids e.g. biological samples such as blood, urine, sweat or saliva or aqueous solutions or suspensions of gases or solids.

The term "analytical device" is to be understood to include analytical test elements, cuvettes or sampling elements such as pipettes or such like.

Analytical devices can be preferably analytical test elements where suitable detection reactions occur already during or after uptake of the sample liquid which allow the determination of the presence or amount of an analyte in the sample. In the sense used here analytical test elements are test elements that can be evaluated visually or optically by means of an apparatus e.g. test strips, biosensors such as enzymatic biosensors or optical biosensors (optrodes, wave conductors etc.), electrochemical sensors and such like. In the analytical test elements enzymatic or immunological methods or methods based on nucleic acids are preferably used for the analyte detection. Analytical devices in the sense of the invention can, however, also be cuvettes or pipettes which are only used to pick up the sample for example by a capillary zone and which either release the sample again or in which the analysis occurs without subsequent reactions. The analytical devices can of course also be used to store and keep sample liquids. Such analytical devices are comprehensively described in the prior art and are familiar to a person skilled in the art in a multitude of embodiments. The following documents are referred to as examples: German Patent Application file number 197 53 847.9, EP-A 0 138 152, EP-A 0 821 234; EP-A 0 821 233, EP-A 0 750 185, EP-A 0 650 054, EP-A-0 471 986, EP-A 0 699 906 and WO 97/02487.

According to the invention the analytical device preferably contains at least two components. The analytical device according to the invention preferably contains a carrier which preferably has a layered structure and is joined to at least one other material with the aid of an adhesive. In the case of a cuvette this second material can be a layer which is identical to the carrier layer and which together with the carrier forms two opposing faces of the cuvette. In the case of an analytical test element the second material can for example be a cover layer, a detection layer, a separation layer for example for particulate sample components that should not penetrate the detection layer, a liquid transport layer, a spreading layer or a layer for taking up excess sample. If there are more than two components it is also possible that the carrier is not joined to another component with the aid of the adhesive but rather than two of the other components such as the separation layer and detection layer are joined by an adhesive. A layered structure in the sense of the invention is intended to include not only flat layers but also curved e.g. corrugated layers.

A number of materials are suitable as carriers for the analytical devices according to the invention that are usually used to manufacture analytical devices such as test elements such as e.g. metal or plastic foils, coated papers or cardboards and, although less preferred, glass. The carrier is preferably manufactured form an opaque or transparent plastic foil for example from polyethylene, polypropylene, polyethylene terephthalate, polystyrene or polycarbonate. Materials known to a person skilled in the art from the prior art are also suitable according to the invention for the other components mentioned above: reagent-impregnated fleeces (cf. e.g. DE-A 196 22 503), papers (cf. e.g. DE-A 27 16 060), membranes (cf. e.g. U.S. Pat. No. 5,451,504) or coating compounds (cf. e.g. DE-A 196 29 656) applied as a film to a support layer are suitable as detection layers; membranes (cf. e.g. DE-A 39 22 495) or fleeces (cf. e.g. EP-A 0 045 476) are suitable as separation layers; chromatographic fleeces (cf. e.g. EP-A 0 339 459), papers (cf. e.g. U.S. Pat. No. 4,861,711), fabrics (cf. e.g. DE-A 196 29 657) or membranes (cf. e.g. U.S. Pat. No. 5,451,504) are suitable as transport layers for the sample liquid or as layers for the uptake of excess sample; fabrics among others which are optionally impregnated with auxiliary substances (cf. e.g. DE-A 196 29 657) are suitable as spreading layers.

An adhesive is used to join two of the at least two components of the analytical device according to the invention. Depending on which type of bond is desired or which assembly technique is used, it is possible to use the adhesive in the form of an adhesive film, an adhesive layer, individual adhesive areas e.g. as a pattern of points or lines, or as a single-sided or double-sided adhesive tape. In addition depending on the type of layers to be joined, the adhesive can be selected from the group of adhesives that set physically which include glues, pastes, solvent-based adhesives, dispersion adhesives and hot-melt adhesives, or adhesives which set chemically. Physically-setting, solvent-containing or solvent-free adhesives are preferably used for the analytical devices according to the invention. Solvent-free, physically-setting adhesives are particularly preferred and these are especially preferred in the form of adhesive tapes, in particular adhesive tapes which have adhesive on both sides. It has turned out that according to the invention in particular adhesive tapes containing acrylate adhesive give excellent results.

A special feature of the analytical device according to the invention is that the adhesive used to join two of the at least two components contains an adsorptive material. Adhesives which in principle contain an adsorptive material such as carbon black or activated charcoal are described in the prior art but without mentioning or making obvious their use according to the invention to stabilize analytical devices which is described here. In JP 56010458 and JP 56010459 activated charcoal is inserted between two layers of partially gas-permeable materials with the aid of a hot-melt adhesive layer and this laminate is used as a packaging material for foods in order to adsorb trace elements from the air which would lead to perishing of fruit and vegetables. Carbon black in adhesives is known for example from DE-A 1594226 to stabilize light-sensitive adhesives, from JP 2011684 for the production of pressure-sensitive adhesives, from Zhongguo Jiaonianji 4 (1995) 31–33 for the production of anti-static adhesives and from EP-A 0 174 188 as a microwave-sensitive additive to adhesives.

It has surprisingly turned out that the presence of an adsorptive material in the adhesive leads to a considerable increase in the stability of the examined analytical devices. Whereas conventional analytical devices which are manufactured using adhesives which contain no adsorptive materials exhibit a considerable deterioration of particular properties with time such as wettability of the areas which come into contact with the sample liquid or integrity of the reagents, these adverse effects can be reduced or even prevented by the addition of adsorptive materials to the adhesive. It is presumed that this stabilizing effect of the adsorbing agent in the adhesive is due to the fact that volatile or migratory substances which impair the stability of the analytical device which are present in the adhesive are retained by the absorbing agent in the adhesive and can either no longer pass over from the adhesive into sensitive regions of the analytical device or are delayed in doing so to a greater or lesser extent. This is all the more surprising since the adsorbing agent is surrounded on all sides by adhesive but nevertheless still retains its adsorptive capacity.

The addition of an adsorptive substance has proven to be advantageous especially for analytical devices which contain a capillary active zone such as a capillary gap or a capillary active fleece, paper or fabric. The presence of a capillary active zone, in particular a capillary gap, enables the automatic uptake of a defined—when the capillary active zone is manufactured sufficiently accurately and reproducibly—sample volume in the analytical devices according to the invention and is therefore preferred. The capillary active zone can be of any shape provided that capillarity is ensured in at least one dimension. In particular the analytical device according to the invention can contain a capillary which is composed of a stiff carrier foil and an optionally identical cover foil which are joined by a spacer layer which incorporates a recess in the shape of a capillary in such a manner that a capillary gap is formed between them. An adhesive tape with adhesive on both sides is preferably used as the spacer layer in which an adsorptive material has been added to the adhesive.

Whereas the filling properties of capillaries in analytical devices which have been produced with conventional adhesives containing no adsorbing agents deteriorate over time, the use of adhesives which contain adsorbing agents as an additive enables the time that is required to fill the capillary in the analytical device with sample liquid to be essentially kept constant even when stored for long periods and at high temperatures. This applies particularly to aqueous sample liquids which are examined with analytical devices in which the capillary active zones are manufactured essentially from nonpolar materials and which are therefore treated with hydrophilizing agents. Apparently certain ingredients of the adhesives abolish or reduce the hydrophilizing effect that increases the wettability of nonpolar surfaces. If adsorbing agents are added to the adhesive as described by the invention, the adverse effect of the said ingredients can be reduced or even abolished. As a result the surfaces of the analytical devices according to the invention remain essentially unchanged and the effect on the capillaries is that the filling time for a capillary produced in this manner remains constant.

Solid substances which are able to selectively concentrate substances from gaseous or liquid mixtures on their boundary surface by physisorption and/or chemisorption have proven to be suitable according to the invention as adsorptive materials or adsorbents or adsorbing agents. The choice of the adsorbent determines which substances can be preferably adsorbed. The more finely a certain amount of the adsorbent is dispersed, the higher is also its adsorptive capacity. Porous solids with rough surfaces are preferred according to the invention e.g. activated charcoals, aluminium oxides, silica gels, carbon blacks or zeolites and it is particularly preferred that these solids are not soluble in the adhesive. Carbon black or activated charcoal is particularly preferred as an adsorbing agent. Preferably only one type of adsorbing agent is admixed with the adhesive. It is, however, also possible to mix mixtures of adsorbing agents with the adhesive which can be optimized by routine experiments.

In order not to unnecessarily influence the adhesive properties and the working properties of the adhesive by the addition of adsorptive materials, it has proven to be advantageous to admix not more than 40% by weight adsorbent relative to the dried total mass of the adhesive. On the other hand the advantageous effect of the adsorbing agent does not occur below 1% by weight. 1 to 30% by weight adsorbent and particularly preferably 5 to 30% by weight adsorbent is preferably added.

The optimal amount of adsorbing agent depends naturally on its type, its inner and outer surface area, its particle size and fine dispersion, and the adhesive power and working properties of the resulting adhesive compound, on the one hand, and the desired stabilizing effect of the adsorbent additive, on the other hand, must be taken into consideration. Optimal weight percentages can be determined by a person skilled in the art by simple experiments.

The analytical devices according to the invention and the use according to the invention of adhesives which contain adsorbing agents have the following advantages:
- Damaging effects of adhesive components on the reagents in the analytical devices according to the invention and in particular in test elements are reduced. This increases the storage stability of the analytical devices according to the invention.
- Adverse effects on hydrophilized regions in the analytical devices are minimized. This stabilizes the wettability of these regions by aqueous sample liquids.

The invention is elucidated in more detail by the following examples and the FIGURE.

FIG. 1 shows an exploded view of a particularly preferred embodiment of an analytical test element according to the invention.

The numbers in the FIGURE denote:
1 carrier layer
2 spacer layer (spacer)
3 capillary active channel
4 recess in the carrier layer
5 detection film
6 cover foil
7 protective foil FIG. 1 shows schematically an exploded view of a preferred embodiment of an analytical test element according to the invention. A spacer layer 2 which determines the contour and the height (corresponding to the thickness of the spacer layer 2) of a capillary active channel 3 is located on a carrier layer 1 in which a recess 4 has been introduced in the shape of a V-shaped notch which among others serves as a marker for the sample application site. The spacer layer 2 is composed of an adhesive tape with adhesive on both sides in which activated charcoal has been added to the adhesive compound. A cover foil 6, a detection film 5 and a protective foil 7 are placed on this spacer layer 2. The cover foil 6 and detection film 5 are mounted so close to one another that the capillary-active zone 3 extends continuously from the free edge of the cover foil 6 resting over the notch 4 up to the opposite free edge of the detection film 5. The recess in the spacer layer 2 which has the shape of a capillary-active channel 3 is slightly longer than the cover foil 6 and the detection element 5 together so that an uncovered gap remains which is usually a few millimeters in width from which air can escape when the capillary-active zone 3 is filled with sample liquid. This gap also remains uncovered by the protective foil 7 to ensure its function is retained. The protective foil 7 should prevent exposed areas of the adhesive tape 2 from leading to an undesired sticking of the test element to objects from the environment.

EXAMPLE 1
Manufacture of an Inventive Analytical Test Element According to FIG. 1

A double-sided adhesive tape with a thickness of 100 $\mu$m which is composed of a 50 $\mu$m thick polyethylene terephthalate foil (Melinex®, ICI, Frankfurt am Main, Germany) which was coated on both sides with a 25 $\mu$m thick layer of adhesive ((Duro-Tak 373-0102, National Starch) to which 30% by weight activated charcoal was added (Pulsorb GW, particle size less than 18 $\mu$m, Chemviron Carbon) relative to the total weight was glued onto a 350 $\mu$m thick foil made of polyethylene terephthalate (Melinex®, ICI, Frankfurt am Main, Germany) coated with a 30 nm thick layer of aluminium which was oxidized completely with water-vapour according to the German Patent Application file number P 197 53 848.7. The foil had a length of 25 mm and was 5 mm wide. A central, notch-shaped recess of 1 mm width and 2 mm length was located on one of the short sides. The adhesive tape had a cut out of 2 mm width and more than 15 mm length which defines the dimensions of the capillary channel. The length of the cut out was slightly larger than the desired length of the capillary active channel which was defined by its covering in order to ensure that air can be vented from the channel during filling with sample liquid. A 3 mm long and 5 mm wide detection film was glued onto the adhesive tape on the side on which the air venting was provided at a distance of 1 mm from the end of the cut out. A film was used as the detection film as is known from DE-A 196 29 656. The detection film was specific for the detection of glucose. A 12 mm long and 5 mm wide cover layer was glued onto the area of the adhesive tape which was still exposed between the notch-shaped recess and detection film so that the cover layer and detection film abutted one another. The cover layer was composed of a 150 $\mu$m thick polyethylene terephthalate foil coated with adhesive on the one side and on which a 6 $\mu$m thick polyethylene terephthalate foil coated with oxidized aluminium as described above with a thickness of 30 nm was glued on the side facing the capillary channel (both: Hostaphan®, Hoechst, Frankfurt am Main, Germany). In order to cover areas of the adhesive tape which were still exposed, this was covered with a 175 $\mu$m thick foil of polyethylene terephthalate (Melinex®, ICI, Frankfurt am Main, Germany) without covering the functional areas.

The test element obtained in this manner had a capillary channel of 15 mm length, 2 mm width and 0.1 mm height. The channel was able to take up 3 $\mu$l sample liquid. The detection film was wetted by the sample over an area of 3 mm×2 mm.

EXAMPLE 2
Time-dependent Filling Properties of Capillaries

Acrylate adhesive (Duro-Tak 373-0102, National Starch) with an addition of 30% by weight activated charcoal (Pulsorb GW, particle size less than 18 $\mu$m, Chemviron Carbon) relative to the total mass of the adhesive was applied in 25 $\mu$m thick layers onto a 50 $\mu$m thick carrier foil made of polyethylene terephthalate (Melinex®, ICI, Frankfurt am Main, Germany) and thus processed into an adhesive tape with adhesive on both sides. A rectangular piece with a size of 2×16 mm² was cut out of a 5×20 mm² piece of the adhesive tape manufactured in this manner so that a symmetrical, U-shaped remnant of adhesive tape remained. This was glued flush onto a 5×20 mm², 350 μm thick, untreated polyethylene terephthalate foil (Melinex®, ICI, Frankfurt am Main, Germany) and the remaining surface was covered with a 5×15 mm², 350 μm thick foil made of polyethylene terephthalate (Melinex®, ICI, Frankfurt am Main, Germany) which had been previously coated on the side facing the adhesive tape with a 30 nm thick layer of aluminium which was completely oxidized with water-vapour according to example 1. The smaller of the two polyethylene terephthalate foils covered with two parallel legs of the U-shaped adhesive tape and were flush with the opening of the U. A rectangular capillary space with dimensions of 2×15×0.1 mm³ was produced in this manner which was open on one side in order to take up liquid. A capillary was manufactured in an analogous manner where the adhesive tape contained no activated charcoal additive.

The capillaries manufactured in this manner with activated charcoal containing and activated charcoal-free adhesive tapes were used to carry out filling experiments with EDTA venous blood (haematocrit 42%). The time was determined which is required by the sample liquid to completely fill the capillary space. The results are summarized in Table 1.

TABLE 1

| Time of measurement | Filling time when using adhesive tap, without activated charcoal additive | Filling time when using adhesive tape with activated charcoal additive |
|---|---|---|
| immediately after manufacture of the capillary | 2.5 s | 2.5 s |
| after 4 weeks storage at room temperature (21–23° C.) | 3.8 s | 2.5 s |
| after 4 weeks storage at 35° C. | >10 s | 2.6 s |

As can be seen in Table 1 the use according to the invention of an adhesive tape containing activated charcoal resulted in a considerable increase in the stability of the capillary at room temperature as well as at an elevated storage temperature.

EXAMPLE 3
Time-dependent Filling Properties of Capillaries Containing Different Adsorptive Materials Capillaries were manufactured in analogy to example 2. In this case the following dried different adsorptive materials were added to the acrylate adhesive (Duro-Tak 373-0102, National Starch):
1.) activated charcoal (Pulsorb GW, Chemviron Carbon)
2.) silica gel
3.) aluminium oxide (G 60 neutral, Merck)
4.) molecular sieve
In all cases the percentage of adsorptive material after drying the adhesive was 15% by weight.

The capillaries obtained in this manner were stored for 3.5 weeks at room temperature (RT), at 35° C. and at 50° C. The filling times determined according to example 2 of the 3.5 week old capillaries were compared with the filling times of a freshly prepared capillary in which only the aluminium oxide coated foil but not the other components were stored at the above-mentioned temperatures. A capillary was used as a reference which contained no addition of an adsorptive material in the adhesive and was also stored for 3.5 weeks at the above-mentioned temperatures. The means of the filling times from 8 measurements in each case are shown in Table 2 for each of the examined capillaries.

TABLE 2

| | filling time (in s) of the capillaries with different additives after 3.5 weeks storage (mean of n = 8 measurements) | | | | | freshly prepared reference capillary |
|---|---|---|---|---|---|---|
| Storage temperature | no additive | activated charcoal | silica gel | aluminium oxide | molecular sieve | |
| RT | >10 | 2.4 | 2.6 | 3.2 | 3.4 | 2.4 |
| 35° C. | >10 | 3.2 | 2.1 | 3.9 | 3.9 | 2.4 |
| 50° C. | >10 | 3.5 | 2.5 | 6.6 | >10 | 2.5 |

What is claimed is:

1. An analytical device adapted for use with sample liquids, said analytical device comprising:

a carrier layer;

at least two functional layers comprising a detection layer, a separation layer constructed of a membrane or fleece, a transport layer, a layer for the uptake of excess sample, or a spreading layer, and an adhesive comprising a porous solid adsorptive material positioned between at least two of said functional layers, wherein at least two of said functional layers are joined together with the aid of the adhesive and wherein said adhesive is formed to join together at least two of said functional layers during contact of the liquid sample with the functional layer.

2. The analytical device of claim 1 wherein the adsorptive material comprises a porous solid.

3. The analytical device of claim 2 wherein the solid is not soluble in the adhesive.

4. The analytical device of claim 2 wherein the solid comprises at least one of an activated charcoal, a carbon black, an aluminium oxide, a silica gel or a zeolite.

5. The analytical device of claim 4 wherein the solid comprises at least one of activated charcoal or carbon black.

6. The analytical device of claim 1 wherein the content of adsorptive material is 1 to 40% by weight relative to the dried total mass of the adhesive.

7. The analytical device of claim 1 wherein the adhesive sets physically.

8. The analytical device of claim 7 wherein the adhesive is solvent-free.

9. The analytical device of claim 8 wherein the adhesive comprises an acrylate adhesive.

10. The analytical device of claim 7 wherein the adhesive is present in the form of an adhesive tape.

11. The analytical device of claim 10 wherein the adhesive tape is adherent on both sides.

12. The analytical device of claim 11 wherein both sides of the adhesive tape are coated identically.

13. The analytical device of claim 1 wherein the analytical device is a test element.

14. The analytical device of claim 1 wherein the analytical device comprises a capillary gap.

15. An analytical device adapted for use with sample liquids, said analytical device comprising
  a carrier layer,
  and at least two functional layers selected from the group consisting of a detection layer, a separation layer constructed of a membrane or fleece, a transport layer, a layer for the uptake of excess sample, and a spreading layer,
  wherein at least two of said functional layers are joined together with the aid of an adhesive,
  wherein the adhesive comprises a porous solid as adsorptive material, and wherein the porous solid comprises at least one of an activated charcoal, a carbon black, an aluminum oxide, a silica gel or a zeolithe,
  and wherein said adhesive is formed to join together at least two of said functional layers during contact of the liquid sample with the functional layer.

16. The device of claim 15 wherein the solid is not soluble in the adhesive.

17. The analytical device of claim 15 wherein the solid comprises at least one of activated charcoal or carbon black.

18. The analytical device of claim 15 wherein the content of adsorptive material is 1 to 40% by weight relative to the dried total mass of the adhesive.

19. The analytical device of claim 15 wherein the adhesive sets physically.

20. The analytical device of claim 15 wherein the adhesive is solvent-free.

21. The analytical device of claim 15 wherein the adhesive comprises an acrylate adhesive.

22. The analytical device of claim 15 wherein the adhesive is present in the form of an adhesive tape.

23. The analytical device of claim 15 wherein the adhesive tape is adherent on both sides.

24. The analytical device of claim 15 wherein both sides of the adhesive tape are coated identically.

25. The analytical device of claim 15 wherein the analytical device is a test element.

26. The analytical device of claim 15 wherein the analytical device comprises a capillary gap.

* * * * *